United States Patent [19]

Sendax

[11] Patent Number: 5,456,601
[45] Date of Patent: Oct. 10, 1995

[54] SINUS DENTAL IMPLANT STABILIZER

[76] Inventor: Victor I. Sendax, 30 Central Park South, Ste. 14B, New York, N.Y. 10019

[21] Appl. No.: 179,785

[22] Filed: Jan. 11, 1994

[51] Int. Cl.⁶ .................................................. A61C 8/00
[52] U.S. Cl. ............................................................ 433/173
[58] Field of Search ......................... 433/172, 173, 433/174, 175, 176; 411/366, 367, 368, 395

[56] References Cited

U.S. PATENT DOCUMENTS

| | | | |
|---|---|---|---|
| 2,258,207 | 10/1941 | Irwin | 433/173 |
| 4,531,916 | 7/1985 | Scantlebury et al. | 433/173 |
| 4,682,951 | 7/1987 | Linkow | 433/173 |
| 4,702,697 | 10/1987 | Linkow | 433/173 |
| 5,104,318 | 4/1992 | Piche et al. | 433/173 X |
| 5,133,662 | 7/1992 | Metcalfe | 433/172 X |

FOREIGN PATENT DOCUMENTS

| | | | |
|---|---|---|---|
| 1211044 | 3/1960 | France | 433/173 |
| 1075793 | 2/1960 | Germany | 433/173 |
| 4036753 | 5/1992 | Germany | 433/174 |
| 0031654 | 2/1988 | Japan | 433/172 |
| 0728855 | 5/1980 | U.S.S.R. | 433/173 |

*Primary Examiner*—Nicholas D. Lucchesi
*Attorney, Agent, or Firm*—Sprung Horn Kramer & Woods

[57] ABSTRACT

A sinus dental implant assembly stabilizer comprising
- (a) an elongated implant having an internal recess at one end,
- (b) an insert removably fitting into said recess, and having a head projecting laterally beyond said recess,
- (c) a washer capable of being removably held in fixed position by said implant and insert, and
- (d) a nut having an opening to fit over said implant of a size and internal configuration so as to be held in position on said implant, said nut holding said nut securely when said implant is being inserted into said nut.

10 Claims, 1 Drawing Sheet

SINUS DENTAL IMPLANT STABILIZER

BACKGROUND OF THE INVENTION

Artificial dentures, in whole or in part, are well-known and work effectively. However, in eating certain types of foods, as well as for other reasons, there are now available means for giving the patient permanent non-removable dentures.

Such permanent dentures are provided by fixing implants to the jaw bone and/or sinus bone of the patient. After some time, the bone in effect becomes one with the implants which then serve as posts to which artificial dentures may be permanently secured, as by screws.

In certain patients the bone at the base of the sinus cavity is too thin to anchor the implant, i.e. efforts to drill into the bone and place the implant result in instability of the implant, defeating the intended purpose.

One way of addressing this problem was to peel back the skin covering the sinus bone, surgically cutting through the sinus bone to form a bone flap secured to cartilage, swinging said flap inwardly to form a lateral window opening (bony infracture window), through said opening introducing a mixture of powered fragments of bone chip and adhesive, restoring the flap to its original position and letting the adhesive set. The mass adheres to the sinus bone and, after a long period of time, through chemical and biological means, the bone particles become one with the sinus bone, producing a thickened sinus bone.

Thus there is formed a "new" sinus bone strong enough to receive the implant in essentially conventional manner.

Thus there are two prolonged time intervals before the implant is ready to receive the dentures.

OBJECT OF THE INVENTION

It is accordingly an object of the present invention significantly to shorten the time needed to effect secure placement of an implant in a patient's thin sinus floor bone.

It is a further object of the invention to effect simultaneously the setting of synthetic particulate bone fragments within the sinus cavity and the stabilizing of the implant in the newly augmented bone.

It is a further object of the invention to provide a novel dental implant assembly which will permit realization of the foregoing objectives.

BRIEF DESCRIPTION OF THE INVENTION

These and other objects are realized in accordance with the present invention pursuant to which there is provided a sinus dental implant stabilizer assembly comprising (a) an elongated implant having an internal recess at one end, (b) an insert removably fitting into said recess, having a head projecting laterally beyond said recess, (c) a washer capable of being removably held in a fixed position by said implant and insert, and (d) a nut having an opening to fit over said implant of a size and internal configuration so as to be held in position on said implant, said nut being provided with means to hold it securely when said implant is being inserted into said nut.

Employing this assembly involves the following steps:

(a) forming a bony infracture lateral window in the sinus bone from outside to within the sinus bone cavity, (b) forming a first essentially vertical opening in the sinus bone from outside to within the sinus bone cavity, (c) holding a nut within said cavity, said nut having a second opening in registry with the first opening in said bone, (d) inserting through said first opening, said sinus bone and second registered opening into said cavity the dental implant of a dental implant assembly so as to secure said implant to said nut, said implant at its end remote from the nut having a recess into which an insert removably fits, said insert having a head projecting laterally beyond said recess, said assembly further including a washer capable of being removably held in fixed position by said implant and insert, the insertion of said implant into the nut held in the sinus cavity continuing until said bone is held between said nut and washer, (e) partially filling said cavity with particulate dental graft material, and (f) restoring the bony infracture lateral window to initial position.

Thereby both essential preliminary features in affixing teeth permanently are effected at the same time rather than serially, saving several months in the overall procedure.

While the invention is particularly applicable to thin sinus floor bone, it can be employed with thicker bone as well, if doubts still remain as to the ability of said bone to hold an implant securely until the graft heals.

The implant of the novel assembly is of conventional configuration.

The assembly is advantageously of titanium, i.e., a strong inert bone-compatible material.

The invention will be further described with reference to the accompanying drawings wherein.

Figure 1:
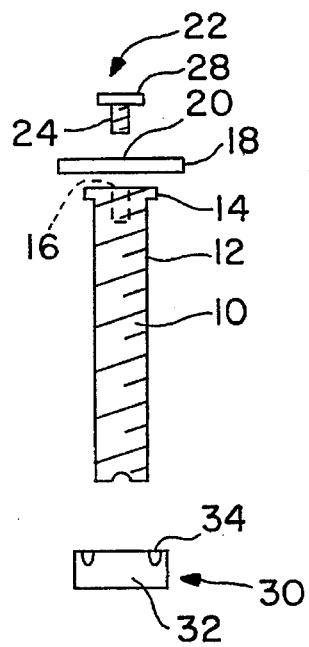
FIG. 1 is an exploded view of a dental implant stabilizer assembly in accordance with the present invention.
Figure 2:
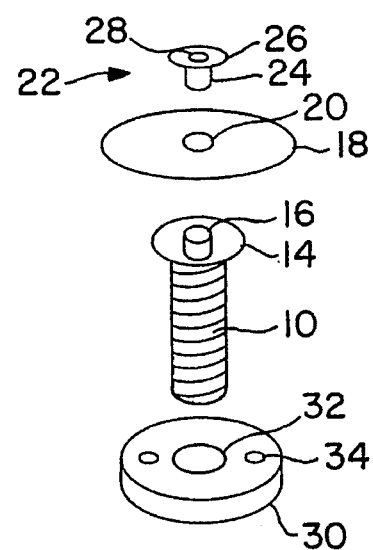
FIG. 2 is a perspective view of the elements of FIG. 1.
Figure 3:
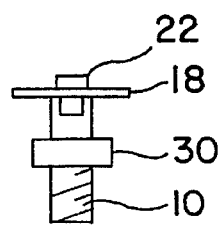
FIG. 3 is a side view of the assembled device, without connection to the patient's bone.

Referring now more particularly to the drawings, in FIGS. 1 to 3 there is shown an assembly comprising a cylindrical implant (or post) 10 approximately one-half inch in length and formed of titanium. The implant 10 is externally threaded at 12. The implant 10 at its upper end has a head 14 of slightly greater diameter than the screw threaded portion 12. In addition, the upper end of implant 10 has an essentially cylindrical internally threaded recess 16 of small diameter.

A washer 18 advantageously of slightly concave-convex configuration to conform more closely to a patient's jawbone dentuous ridge, has a central opening 20 only slightly larger in diameter than recess 16, the washer being larger in diameter than head 14.

An insert 22 has a threaded post 24 of a size securely to mate with recess 16 of head 14 of implant 10. The insert 22 has a laterally projecting head 26. The top of said head has a hexagonal recess 28 (FIG. 2) by means of which a tool (not shown) can thread it into (FIG. 3) or remove it from internally threaded recess 16. Such insert 22 is known in the art as a healing or cover screw.

Finally, there is a nut 30 which is internally threaded at 32. The top of nut 30 has two diametrically opposite deep channels or holes 34 by means of which a two-pronged tool, e.g. a forceps (not shown), can hold it stationary while the implant 10 is threaded through the nut so as to increase or reduce the distance between the nut 30 and top 14.

FIG. 3 shows the assembled device, not yet connected to a patient's sinus bone.

Figure 4:
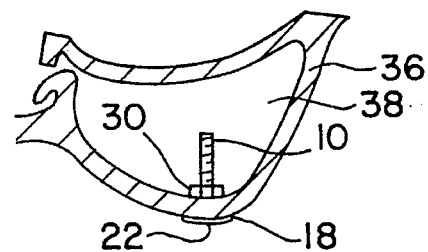
FIG. 4 is a sectional view of the sinus bone of a patient's mouth with the device implanted and the sinus cavity partially filled to effect setting of the implant.

Referring now to FIG. 4, in use the dentist in conventional manner forms a bony infracture lateral window (now shown) through the patient's sinus bone 36.

He then drills through the sinus bone 36 into the sinus cavity 38 forming a first opening in the sinus bone ultimately to hold implant 10. Through the lateral window he then puts nut 30 into the cavity 38 with its opening in registry with the first opening in the sinus bone.

The dentist holds the nut 30 in position by means of a forceps fitting into channels 34 in the nut thereby holding the nut in position while preventing it from rotating. Implant 10 is inserted through the first opening in the sinus bone and threaded into the opening in nut 30, thereby engaging it.

Implant 10 carries washer 18 and insert 22. The hexagonal recess 28 helps to effect the threading by means of an appropriate hex-ended tool fitting into recess 28. Threading the implant into position stops when washer 18 engages the sinus bone.

The sinus cavity is partially filled with bone fragments in known manner, the bony infracture lateral window is restored to its initial original position and the procedure is essentially finished. In a month or more the bone fragments become one with the bone and at the same time the implant becomes one with the bone, whereas heretofore these were effected serially, thus taking much longer overall.

When finished, the dentist simply removes insert 22 by screwing it out so the recess 16 is available for receiving permanent denture posts in conventional manner.

Figure 5:
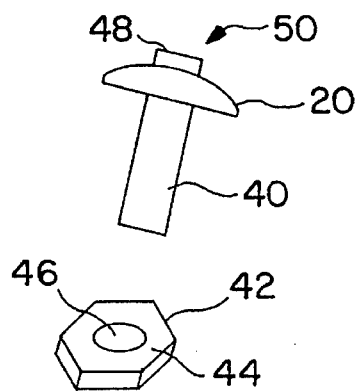
FIG. 5 is a perspective view of a modified elongated implant and nut.

In FIG. 5 there is shown an alternate implant assembly comprising an implant 40 and a nut 42 which is hexagonal in external contour so it can be held that way, in contrast with channels 34 of nut 30. In addition, it has notches 44 in its periphery which provide additional or alternative ways of holding the nut 42 while threading the implant 40 into it. The nut 42 merely has a cylindrical opening 46 rather than an internal thread. Instead of screwing the implant into the nut, the implant is physically forced into the opening 46 to engage it by friction.

The insert 48, in place of a hexagonal recess 28 as in FIG. 2, has a simple cross-slot 50 by means of which it can be turned by a screw driver (not shown).

To facilitate lodging of the implant 40 in the nut, the opening 46 can even be a little larger than necessary and any play between implant and opening eliminated by forcing in bone graft fragments. Still another possibility is to provide in the nut a slit from the opening to the outside perimeter, in the manner of a C clip; then the implant can easily be placed and, thereafter the nut squeezed laterally, taking advantage of the play afforded by the slit. In yet another possibility, the nut opening could be slightly off-round to provide some extra play for insertion of the implant while still gripping it once inserted.

By contrast with the system shown in FIG. 4, prior to the present invention the particulate bone fragments were placed into the sinus bone cavity, permitted to become one with the sinus bone, and then the implant was placed into the bone without nut or washer. However, at the end of the process, either old or new, one has the implant protecting outward from the bone, i.e. in the new systems the inserts 22 and 48 are unscrewed and their washers are removed so that visibly the new and old systems are the same. With the new systems there is a nut 30 or 42 embedded in the sinus bone but it poses no problem.

In accordance with another aspect of the present invention the nut 30 or 42 is coated with a thin layer of hydroxyapatite, of the order of about 50 microns in thickness. Such coating encourages osteogenesis around the nut. Thus the bone will fuse to the nut as well as to the implant, resulting in enhanced structural support and strength.

It will be appreciated that the instant specification and claims are set forth by way of illustration and not limitation, and that various modifications and changes may be made without departing from the spirit and scope of the present invention.

What is claimed is:

1. A sinus dental implant assembly stabilizer comprising
   a) an externally threaded elongated implant having an internal recess at one end,
   b) an insert removably fitting into said recess, and having a head projecting laterally beyond said recess,
   c) a washer capable of being removably held in fixed position by said implant and insert, and
   d) a nut having an opening to fit over said implant of a size and internally threaded for engagement with said implant, said nut being provided with means to hold said nut securely when said implant is being inserted into said nut.

2. An assembly according to claim 1, wherein said internal recess of said implant is internally threaded, the head of said insert having means to screw said insert into said implant and further to screw said implant into said nut.

3. An assembly according to claim 1, wherein said washer is slightly concave-convex.

4. An assembly according to claim 1, wherein said nut is coated with hydroxyapatite.

5. A method of fixing a dental implant into a cavity bounded by sinus bone and tissue wherein the cavity is filled with particulate dental graft material which eventually is replaced by bone secured to the sinus bone, and placing a dental implant in said cavity for affixation to said bone, which comprises
   a) forming a bony infracture lateral window in the sinus bone from outside to within the sinus bone cavity,
   b) forming a first essentially vertical opening in the sinus bone from outside to within the sinus bone cavity,
   c) holding a nut within said cavity, said nut having a second opening in registry with the first opening in said bone,
   d) inserting through said first opening and second registered opening the dental implant of a dental implant stabilizer assembly so as to secure said implant to said nut, said implant at an end having a recess into which an insert is removably fitted, said insert having a head projecting laterally beyond said recess, said assembly further including a washer capable of being removably held in fixed position by said implant and insert, the insertion of said implant continuing until said bone is held between said nut and washer,
   e) partially filling said cavity with particulate dental graft material,
   f) restoring the bony infracture lateral window to an initial position,
   g) allowing the structure to set for a prolonged period of time, and h) thereafter removing from the end of said implant the inserted washer, whereby the formation of bone within said cavity and affixation of said implant to such formed bone are effected simultaneously.

6. The method according to claim 5, wherein said insert is externally threaded and said internal recess of said implant is threaded.

7. The method according to claim 5, wherein said implant is externally threaded and said opening in said nut is internally threaded for engagement with said implant.

8. The method according to claim 5, wherein said washer is slightly concave-convex.

9. The method according to claim 5, wherein said implant is externally smooth and said nut opening is internally smooth but they are of a size to effect frictional locking when the implant is forced into said nut opening.

10. The method according to claim 5, wherein said nut is coated with hydroxyapatite.

* * * * *